United States Patent [19]

Fang

[11] Patent Number: 5,293,873
[45] Date of Patent: Mar. 15, 1994

[54] MEASURING ARRANGEMENT FOR TISSUE-OPTICAL EXAMINATION OF A SUBJECT WITH VISIBLE, NIR OR IR LIGHT

[75] Inventor: Ming Fang, Plainsboro, N.J.

[73] Assignee: Siemens Aktiengesellschaft, Munich

[21] Appl. No.: 935,281

[22] Filed: Aug. 26, 1992

[30] Foreign Application Priority Data

Aug. 29, 1991 [DE] Fed. Rep. of Germany ....... 4128744

[51] Int. Cl.[5] ............................................. A61B 8/00
[52] U.S. Cl. .................................... 128/664; 128/665; 128/661.07; 250/339
[58] Field of Search ............................. 126/633-634, 126/664-667, 661.04, 660.04; 356/39-41; 250/339; 128/661.07

[56] References Cited

U.S. PATENT DOCUMENTS

| | | | |
|---|---|---|---|
| 4,515,165 | 5/1985 | Carroll | 128/664 |
| 4,890,619 | 1/1990 | Hatschek | 128/633 |
| 5,007,428 | 4/1991 | Watmough | 128/664 X |
| 5,174,298 | 12/1992 | Dolfi et al. | 128/665 |
| 5,179,951 | 1/1993 | Knudson | 128/633 |

OTHER PUBLICATIONS

"Cerebral Oxygenation Measuring System NIR-1000 (Tentative Data)," Hamamatsu Photonics K.K. System Division (Sep. 1987).
Brochure of Somanetics Corp. for INVOS ™ Mammography System.
"Cerebral Monitoring in Newborn Infants by Magnetic Resonance and Near Infrared Spectroscopy," Delpy et al., Departments of Medical Physics and Bioengineering, Pediatrics and Physiology, University College London.
"Estimation of Optical Pathlength Through Tissue from Direct Time of Flight Measurement," Delpy et al., Phys. Med. Biol., 1988, vol. 33, No. 12, pp. 1433-1442.
"Principles and Practice of Laser-Doppler Anemometry," Durst et al., 1976, pp. 1-13.
"'Son et lumière': A New Combined Optical and Doppler Ultrasound Approach to the Detection of Breast Cancer," Watmough et al., J. Biomed. Eng., vol. 10, Apr. 1988, pp. 119-123.
"Speckle Interferometry," Ennos, from Laser Speckle and Related Phenomenon, Dainty, Ed. 1984, pp. 203-253.
"In vivo Measurement of Breast Composition Using Optical Spectroscopy"; Egan et al.
"Diaphanography with Ultrahigh Speed Imaging"; pp. 2-6; Sep. 1986.

*Primary Examiner*—Angela D. Sykes
*Attorney, Agent, or Firm*—Hill, Steadman & Simpson

[57] ABSTRACT

An apparatus and method for optically analyzing tissue in a subject directs coherent light and ultrasound at the subject along parallel propagation paths. The ultrasound causes a Doppler shift in the light emerging from the subject, this shift being related to certain tissue characteristics. The light emerging from the subject is detected and a corresponding signal is supplied to an evaluation stage which absolutely or relatively calculates the intensity of those parts of the detected light which proceeded through tissue not charged by ultrasound and those parts of the detected light which proceeded through tissue charged by ultrasound.

47 Claims, 3 Drawing Sheets

MEASURING ARRANGEMENT FOR TISSUE-OPTICAL EXAMINATION OF A SUBJECT WITH VISIBLE, NIR OR IR LIGHT

BACKGROUND OF THE INVENTION

1. Field of the Invention

The present invention is directed to a tissue-optical measuring arrangement for the examination of a living subject with visible, NIR or IR light. The wavelength of the visible light lies between 380 and 780 nm, that of NIR light (near infrared light) lies between 780 nm and 1.5 μm and that of IR light (infrared light) lies between 1.5 μm and 1 mm. It is particularly the range from 1.5 μm through 15 μm that is of significance in the present invention given the employment of IR light.

2. Description of the Prior Art

Many optical properties of tissue such as, for example, the absorption, the scattering (dispersion) and the spectral properties can be identified by exposing the tissue to light of the aforementioned wavelength ranges and analyzing the transmitted and/or reflected light. For example, it is possible to identify tissue modifications in mammary diagnostics or to acquire information about the blood supply of the brain in pediatrics and/or neurology by detecting light of the aforementioned wavelength ranges into the respective subject, for example a mammary gland or a skull, detecting the light emerging from the subject and interpreting the information acquired in this way in a suitable way. It is thereby advantageous that these are usually non-invasive procedures. Further details can be derived, for example, from the publications "Cerebral Oxygenation Measuring System NIR-100" (Tentative Data), Hamamatsu Photonics K.K., System Division, September 1987; "INVOS-In Vivo Optical Spectroscopy", Somanetics Corporation, USA; and "Cerebral Monitoring in Newborn Infants by Magnetic Resonance and Near Infrared Spectroscopy", D. T. Delpy et al., Departments of Medical Physics and Bioengineering, Pediatrics and Physiology, University College London.

Unfortunately, the light emerging from the subject that is to be detected in such procedures, which can be back-scattered (diffusely reflected) light or transmitted, dispersed, light contains information about the entire region of the subject illuminated with the incoming light. The measurement is thus not location-selective. This means that one does not known what path the detected light took in the subject and/or cannot determine from what depth of the subject the detected light was reflected. Additionally, in the case of detecting the back-scattered light, most of the light back-scattered from the surface of the subject and the surface-proximate regions thereof must also be measured. This leads to a poor signal-to-noise ratio of the measurement, so that smaller regions which deviate in terms of their optical properties from the surrounding tissue such as, for example, nascent tumors, cannot be recognized. This also applies in the case of detection of the light transmitted through the subject, since the signal-to-noise ratio deteriorates with increasing thickness of the subject to the point that the results are unusable.

Heretofore, essentially only one method has been fundamentally suitable for employment in vivo that offered an incipient solution to these problems. This method, described in the article "Estimation of Optical Pathlength through Tissue from Direct Time of Flight Measurement", D. T. Delpy et al., Phys. Med. Biol., 1988, vol. 33, No. 12, pp. 1433-1442, is based on the "time of flight" measuring principle using a pulsed laser as a light source and an ultra-fast streak camera as the detector means. The pulse duration of the laser is typically less than 1 picosecond. The cronological resolution of the streak camera lies on the order of magnitude of approximately 2 picoseconds. Since the light is back-scattered from the subject to be examined in different depths, or penetrates the subject on different paths, the individual parts of the back-scattered or transmitted light have different arrival times at the streak camera. The detected light parts can thus be selected and detected according to arrival time and, thus, according to the depth in the subject from which they were back-scattered, or the path which they took through the subject. A time of flight measuring system having an adequate chronological resolution and, thus, an adequate topical resolution, however, is expensive.

SUMMARY OF THE INVENTION

It is an object of the invention to provide a tissue-optical measuring arrangement that is simply and economically constructed which nonetheless operates topically selective.

This object is achieved in accordance with the principles of the present invention in a tissue-optical measuring arrangement for the examination of a living subject with visible, NIR or IR light wherein the subject is simultaneously charged with ultrasound, and an evaluation stage calculates the relative or absolute intensities of a portion of the light passing through tissue charged with ultrasound and a portion passing through tissue not charged with ultrasound. The invention thereby makes use of the fact that light that is scattered at a moving subject experiences a frequency shift due to the Doppler effect, a fact which, for example, is also utilized in laser Doppler anemometry (see, for example, "Principles and Practice of Laser-Doppler Anemometry", F. Durst et al., Academic Press, 1976, Chapter 1). In accord therewith, those parts of the detected light that have passed run through tissue charged with ultrasound have a frequency shift compared to the other parts of the detected light. This results in the light emerging from the subject that is detected with a detector means, being in the form of an optical beat signal, i.e., an optical signal with beats. The frequency response function thereof is dependent on the amplitudes of the two light signals forming the optical beat signal.

In the context of the present invention, this permits the evaluation stage to form the relative intensities of that part of the detected light that proceeds to the detector means through tissue not charged by ultrasound and that part of the detected light that proceeds to the detetor means from the light source through tissue charged by ultrasound on the basis of the frequency response function of the signal supplied to the evaluation stage from the detector means. For example, the evaluation stage can form the quotient of the two parts of the detected light. Given suitable calibration of the measuring arrangement, the absolute intensities of the two parts of the detected light can also be determined. Quantitative statements about the respective absorption coefficients are even possible. Location-sleeve measurements are thus possible with the arrangement of the invention. The topical resolution that can thereby be achieved is ultimately dependent upon how "sharply" the region of the subject charged by the ultrasound and the region of the subject not charged by the ultrasound are limited from one another along the main propagation paths of the light and of the ultrasound. It is evident that a region "charged with ultrasound" and a region "not charged with ultrasound" cannot exit in the literal sense since, as is known, an acoustic field is generated upon the introduction of ultrasound into a subject, this sound field, for example, being describable by the locally existing intensity of the ultrasound. One must recognize in the case of the invention that the intensity of the ultrasound in the region of the main propagation path of the light will be greater than zero. That region wherein the intensity of the ultrasound is so slight that light passing through this region exhibits no detectable frequency shift is nonetheless to be considered (defined) as "not charged by ultrasound." The term "main propagation path" as used herein means the respective propagation path on which the light or the ultrasound would propagate without the appearance of dispersion and diffraction phenomena. It is clear that the measuring arrangement of the invention is constructed technologically simply and economically in comparison to the known arrangement based on the time of flight measuring principle. It is self-evident that the dimensions of the ultrasound sources are selected such that they emit the ultrasound in directed fashion. Although it is known from the article "'Son et lumiere' a new combined and doppler ultrasound approach to the detection of breast cancer", D. J. Watmough et al., J. Biomed. Eng., vol. 10, Apr., pp. 119-123 to employ optical diagnostics and ultrasound diagnostics in combination, this is in the context of two separate diagnostic procedures that are independent of one another and that are applied in chronological succession and are intended to mutually support their indications.

In a preferred embodiment of the invention, the evaluation stage forms a quotient of the two intensities, as mentioned above. As a consequence of the fact that a substantially ultrasound-free zone is present through which the main propagation path of the light proceeds, a relatively "sharply" limited region of the subject traversed by the detected light and not charged by ultrasound can be realized. The cross section thereof transversely relative to the main propagation paths (which define the topical resolution that can be achieved) is practically dependent only on the arrangement of the ultrasound sources. An annular arrangement of the ultrasound sources is particularly expedient since a clear limitation of the ultrasound-free zone then results. The term "annular" is used herein to mean that the ultrasound sources are arranged along a closed line having an arbitrary, for example circular or quadratic shape. Advantageously, however, there is also the possibility to provide an annularly fashioned ultrasound source, whereby the term "annular" here is also to be understood in a broad sense, i.e. not only in the sense of circularly annular. An annularly fashioned ultrasound source offers the advantage that the ultrasound-free zone is surrounded by a gap-free space charged with ultrasound, i.e. an especially high topical resolution can be achieved. In a further embodiment, a sound absorber can be disposed against the surface from which the ultrasound exits the subject, so that essentially no reflections occur at that surface. Rather, a significant part of the ultrasound proceeding to the surface is introduced into the sound absorber and is converted into heat therein. This considerably reduces the risk that ultrasound will proceed into the ultrasound-free zone as a consequence of reflections at the surface of the subject. The comments with respect to the "zone not charged with ultrasound" apply analogously to the so-called "ultrasound-free zone", i.e., this means a zone wherein the intensity of the ultrasound is so low within the ultrasound-free zone that the light passing through the zone exhibits no detectable frequency shift.

The light source is preferably a laser diode. The entering and exiting light can be contained in respective light guides so as to be supplied disturbance-free to the subject being examined and so the light emerging from the subject can be supplied disturbance-free to the detector means. The detector means is preferably a photodiode or a photomultiplier. The light guide can be formed in a technologically simple and economic manner with fiber-optics, for example light waveguides such as optical fibers or optical fiber cables.

Further embodiments offer the advantage that larger regions of the subject can be covered, which permits identification of absorption arrays. In an embodiment operating in transmission mode the light and the ultrasound transmitters and detectors are disposed on opposite sides of the subject, and the subject and these transmitters and detectors are relatively moveable. In an embodiment operating in reflection mode the transmitter and detectors are disposed in close proximity and again relative movement is provided. Whether the adsorption arrays are two-dimensional or three-dimensional absorption arrays is dependent on the scan motion executed. The absorption arrays identified in this matter can be visually displayed.

Measuring arrangements according to further embodiments make it possible to identify absorption arrays for different wavelengths, which is important for spectroscopic examination.

DESCRIPTION OF THE PREFERRED EMBODIMENTS

Figure 1:
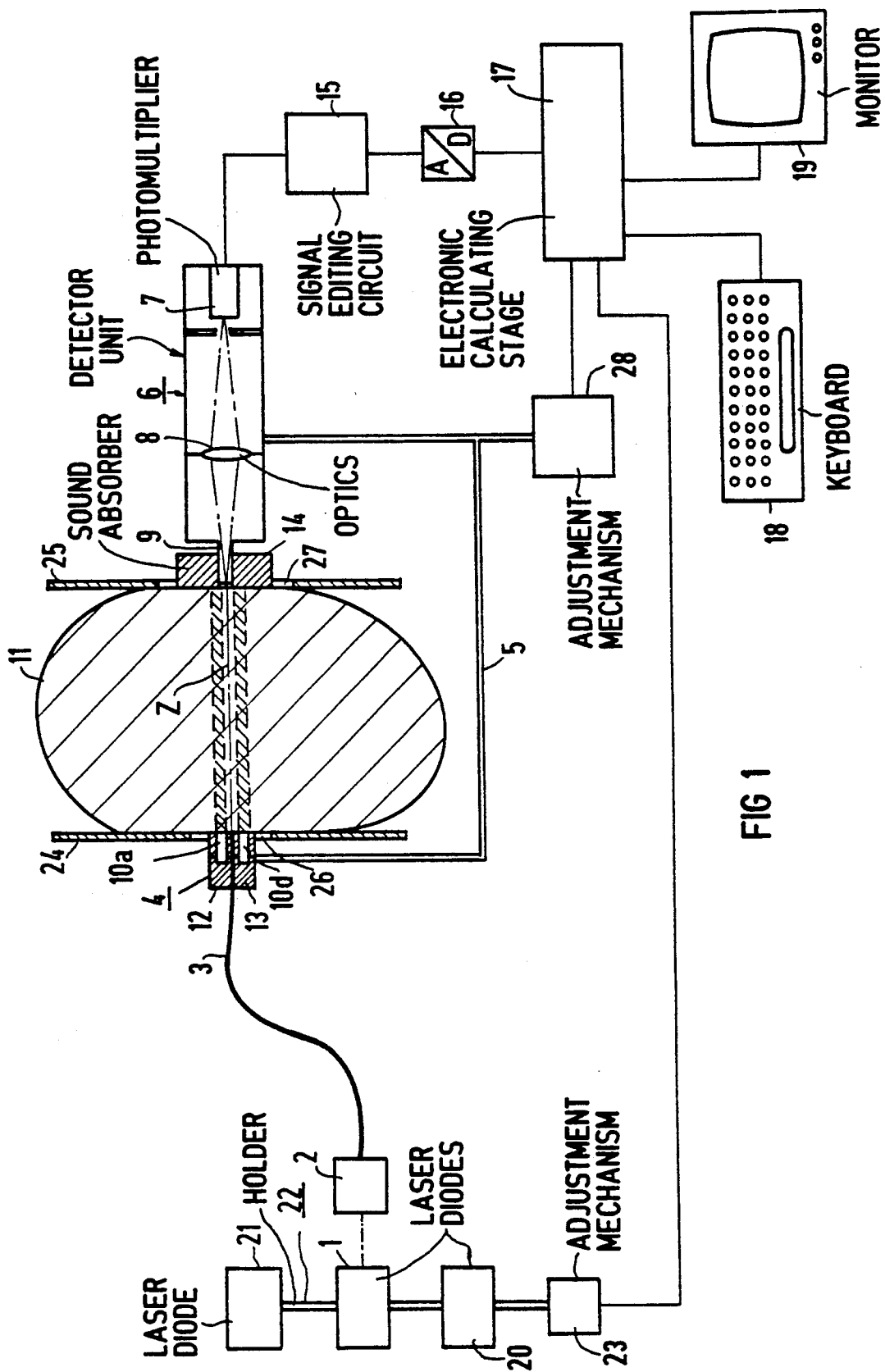
FIG. 1 shows a measuring arrangement of the invention working according to the transmission principle and shown as a block circuit diagram.

The measuring arrangement according to FIG. 1 includes an essentially monochromatic light source connected to a supply unit (not shown). This light source, for example, may be a laser diode 1 that emits coherent light having a wavelength of, for example, 840 nm. The light of the laser diode 1 proceeds to an optical fiber coupler 2 with which it is coupled into a flexible optical fiber 3. The optical fiber 3 leads to an application head generally referenced 4 that is attached in a rigid frame 5. A detector head generally referenced 6 is likewise attached in the frame 5. The detector head 6 contains a detector unit formed of a photomultiplier 7 having a preceding optics 8. The application head 4 and the detector head 6 are attached such to the frame 5 such that the light exit end of the optical fiber 3, forming the light exit zone of the measuring arrangement, and the tubular entrance opening 9 of the detector head 6 acting as a scattered radiation diaphragm, are aligned so that, given the absence of a subject between application head 4 and detector head 6, the light emanating from the optical fiber 3 passes centrally through the entrance opening 9 of the detector head 6 forming the light entry zone of the measuring arrangement, as shown with dot-dash lines in FIG. 1, and proceeds through the optics 8 to the photomultiplier 7. A schematically indicated diaphragm precedes the photomultiplier 7.

Figure 2:
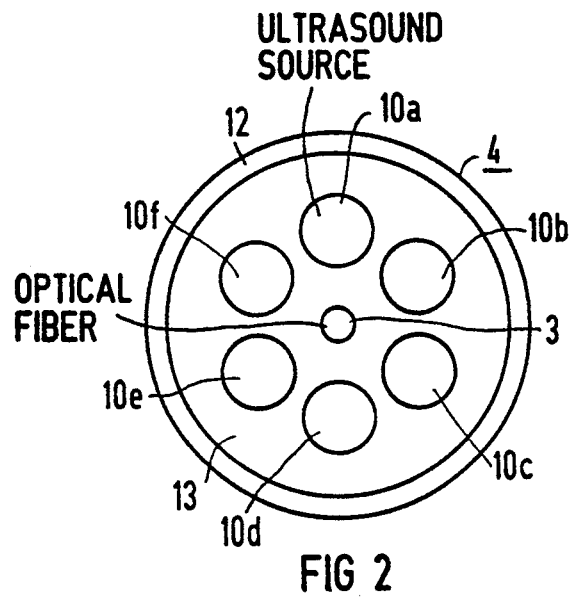
FIG. 2 shows a detail of the arrangement according to FIG. 1.

The application head 4, whose end face provided for seating against the subject 11 to be examined, for example a female breast, is shown in FIG. 2, contains the light exit end of the optical fiber 3 which extends up to this end face. The end face additionally contains six ultrasound sources $10a$ through $10f$ that are arranged distributed at intervals of 60° along the circumference of a circle having a center in which the optical fiber 3 is situated. The application head 4 has pot-shaped housing 12 that is filled with a suitable casting compound into which the optical fiber 3 and the ultrasound sources $10a$ through $10f$ are embedded. The ultrasound sources $10a$ through $10f$ are connected to a generator (in a way not shown) that drives them to generate ultrasound having a frequency of, for example, 5 MHz. The ultrasound sources $10a$ through $10f$ may be for example, piezo oscillators, and have respective emission faces that press against the subject 11 to be examined. Each emission face has a diameter, taking the wavelengths of the emitted ultrasound in the subject 11 into consideration, so that it emits ultrasound in a directed fashion, namely such that the ultrasound mainly propagates in substantially rotationally symmetrical zones of the subject 11 that are parallel to the main propagation path of the light (indicated with dot-dash lines) emanating from the optical fiber 3. The optical fiber 3 has a diameter substantially corresponding to that of an emission face of an ultrasound source $10a$ through $10d$. An ultrasound-free zone Z extending from the light exit end of the optical fiber 3 to the entry opening 9 of the detector head 10 is then present in the subject 11, this ultrasound-free zone Z being annularly surrounded by six regions that are charged by ultrasound. The regions charged by ultrasound and visible in FIG. 1 are indicated by dashed, straight, parallel limiting lines and by a different type of shading. It is self-evident that the regions charged by ultrasound do not have a cylindrical shape in reality but have the shape typical of the acoustic field of ultrasound sources emitting in directed fashion.

In order to prevent ultrasound from proceeding into the ultrasound-free zone Z due to reflection at that side of the subject 11 facing away from the therapy head 4, an annular sound absorber 14 that presses against the surface of the subject 11 is put in place on the detector head 6 in the region of the entry opening 9. Suitable sound absorbers have an acoustic impedance in the region of the surface against the subject 11 that is matched to that of the subject 11, with this acoustic impedance gradually diminishing with increasing distance from the subject 11 to the acoustic impedance of the surrounding air in the ideal case. Such sound absorbers are known from ultrasound technology.

After having been amplified as needed (the amplifying components not being shown) the electrical output signal of the photomultiplier 7 proceeds to an analog-to-digital converter 16 whose digital output data are supplied to an electronic calculating stage 17. The calculating stage 17 has a keyboard 18 serving the purpose of operating the measuring arrangement and a monitor 19.

The functioning of the described measuring arrangement is based on the fact that, as a consequence of the tissue of the subject 11 being an optically turbid or opaque medium, only a slight part of the light detected with the detector head 6 proceeds to the entry opening 9 of the detector head 6 without having left the ultrasound-free zone Z, as a consequence of the dispersion phenomena that occur to a great degree in turbid media. There is an extremely high probability that those parts of the light detected with the detector head 6 that have left the ultrasound-free zone Z will again be scattered in one of the regions that are charged with ultrasound with the ultrasound sources $10a$ through $10f$. Since the regions of the subject 11 charged with ultrasound are not at rest but oscillate due to the ultrasound, those parts of the detected light that were scattered or dispersed in the regions charged with ultrasound exhibit a frequency shift based on the Doppler effect in comparison to those parts of the detected light that have not left the ultrasound-free zone Z. An optical beat signal thus enters the detector head 6, this optical beat signal arising due to the superimposition of the light scattered in the regions charged with ultrasound with that light did not leave the ultrasound-free zone Z.

This optical beat signal proceeds to the photomultiplier 7 through the optics 8, which has a magnification of the subjective speckle size which is adequate for the detection with the photomultiplier 7 (in this respect, see "Speckle Interferometry", A. E. Ennos, in "Laser Speckle and Related Phenomenon", Editor J. C. Dainty, Springer-Verlag, 1984, pp. 203 through 253). The output signal of the photomultiplier 7, can be considered as corresponding to the demodulated beat light signal, i.e. it reproduces the curve of the frequency response function of the beat light signal. Since, as is known, the amplitudes of the two original signals superimposed to form the beat signal can be identified from the frequency response function, or from the minimum and maximum amplitude, of a beat signal, the output signal of the photomultiplier thus at least contains information about the quotients of the intensities of the two parts of the detected light superimposed to form the optical beat signal. Given suitable calibration of the measuring arrangement, the intensities of the two parts of the detected light and thus absorption coefficients can also be calculated. Both the quotient formation as well as (potentially) the calculation of the intensities and/or absorption coefficients ensues with the electronic calculating stage 17 to which the output signal of the photomultiplier 7, digitized with the analog-to-digital converter 16, is supplied. The corresponding values are displayed on the monitor 19.

With the measuring arrangement of the invention, thus, it is possible to make statements with respect to the absorption behavior at the wavelength of the light generated with the laser diode 1 in a region that is exactly defined with respect to its position in the subject 11, namely the ultrasound-free zone Z. The topical resolution that can be achieved is thereby only dependent on the cross sectional area of the ultrasound-free zone Z, which is at a right angle relative to the main propagation direction of the light and ultrasound.

In order to be able to understake spectroscopic examinations, laser diodes 21 and 20 that each generate coherent, monochromatic light at respective wavelengths deviating from the wavelength of the light generated with the laser diode 1 are provided in addition to the laser diode 1. The laser diode 20, for example, generates light having a wavelength of 760 nm and the laser diode 21 generates light having a wavelength of 800 nm. The laser diodes 1, 20 and 21 are attached to a holder generally references 22 that is adjustable with an adjustment mechanism 23, controlled by the electronic calculating means 17 such that the light of the laser diode 20 or the laser diode 21 can also be coupled into the optical fiber 3 with the optical fiber coupler 2. The respective laser diode thus coupled-in is activated (in a way not shown) to output light controlled by the electronic calculating stage 17. There is then the possibility of investigating the absorption behavior of the ultrasound-free zone Z in the above-described way for different light wavelengths.

As may be seen from FIG. 1, the subject 11 is pressed between two compression plates 24 and 25. The compression plates 24 and 25 have respective openings 26 and 27 through which the application head 4 or the sound absorber 14 engages the subject 11. The surface of the subject 11 which is accessible through the openings 26 and 27 is essentially flat as a consequence of the compression. The openings 26 and 27 are dimensioned such that the therapy head 4 and the detector head 6 together with the sound absorber 14 can be adjusted in common relative to the subject 11. An adjustment mechanism 28 acting on the frame 5 serves this purpose. This adjustment mechanism 28, and the adjustment mechanism 23 as well, are controlled by the electronic calculating stage 17. The adjustment mechanism 28 allows the application head 4 in common with the detector head 6 together with the sound absorber 14 to be adjusted along a first axis that proceeds perpendicular to the plane of the drawing, and along a second axis that proceeds parallel to the planes of the compression plates 24 and 25 and preferably intersects the first axis at a right angle. The electronic calculating stage 17 drives the adjustment mechanism 28 such that it adjusts the application head 4 and the detector head 6 together with the sound absorber 14 for the purpose of executing a scan motion relative to the subject 11. This scan motion, for example, can arise by first displacing the frames step-by-step in, for example, ten steps through a defined overall dimension that, for example, corresponds to ten times the step distance. This displacement occurs in one direction along the first axis. Subsequently, the frame 5 is displaced by one step along the second axis, with the step distance preferably corresponding to the step distance in the displacement along the first axis. The frame 5 is now adjusted again step-by-step along the first axis by the defined overall dimension but in the other direction. After the displacement by the defined dimension has been carried out, another step-by-step displacement of the frame 5 in the direction of the second axis ensues, i.e., in the same direction as previously. These procedures are repeated until the frame has also been displaced by a defined overall dimension in the direction of the second axis, which for examples, can likewise correspond to ten times the step distance. The step distances, for example, can correspond to the maximum expanse of the cross section of the ultrasound-free zone Z in the direction of the respective axis.

If the examination is to be only undertaken for light of one wavelength, the corresponding laser diode is adjusted before the beginning of the scan motion. This adjustment is undertaken by suitable actuation of the adjustment mechanism 23 so that the light of the selected laser diode is coupled into the optical fiber 3 in every position that the frame 5 assumes in the scan motion. The corresponding laser diode is activated and the output signal of the photomultiplier 7 derived therefrom is evaluated in the above-described way with the electronic calculating stage 17. If the examination is to be implemented for a plurality of wavelengths, the corresponding photodiodes are adjusted successively for every position of the scan motion, by a suitable actuation of the adjustment mechanism 23, so that their light is incident into the optical fiber coupler 2. The corresponding photodiodes are then activated to output light and the output signals of the photomultiplier are evaluated with the electronic calculating stage 17. On the basis of the wavelength at which the data were identified, the electronic calculating stage 17 initially allocates the data to a plurality of data sets corresponding in number to the plurality of wavelengths employed in the measurement, each of these data sets representing an absorption array belonging to a specific wavelength. The corresponding data can be numerically displayed on the monitor 19. The electronic calculating stage 17, however, also assigns different chromatic or grayscale values to the different quotients or absorption coefficients of an adsorption array and to display the corresponding image on the monitor 19. The images obtained in this way are "shadowgraphs" obtained by parallel projection.

Figure 3:
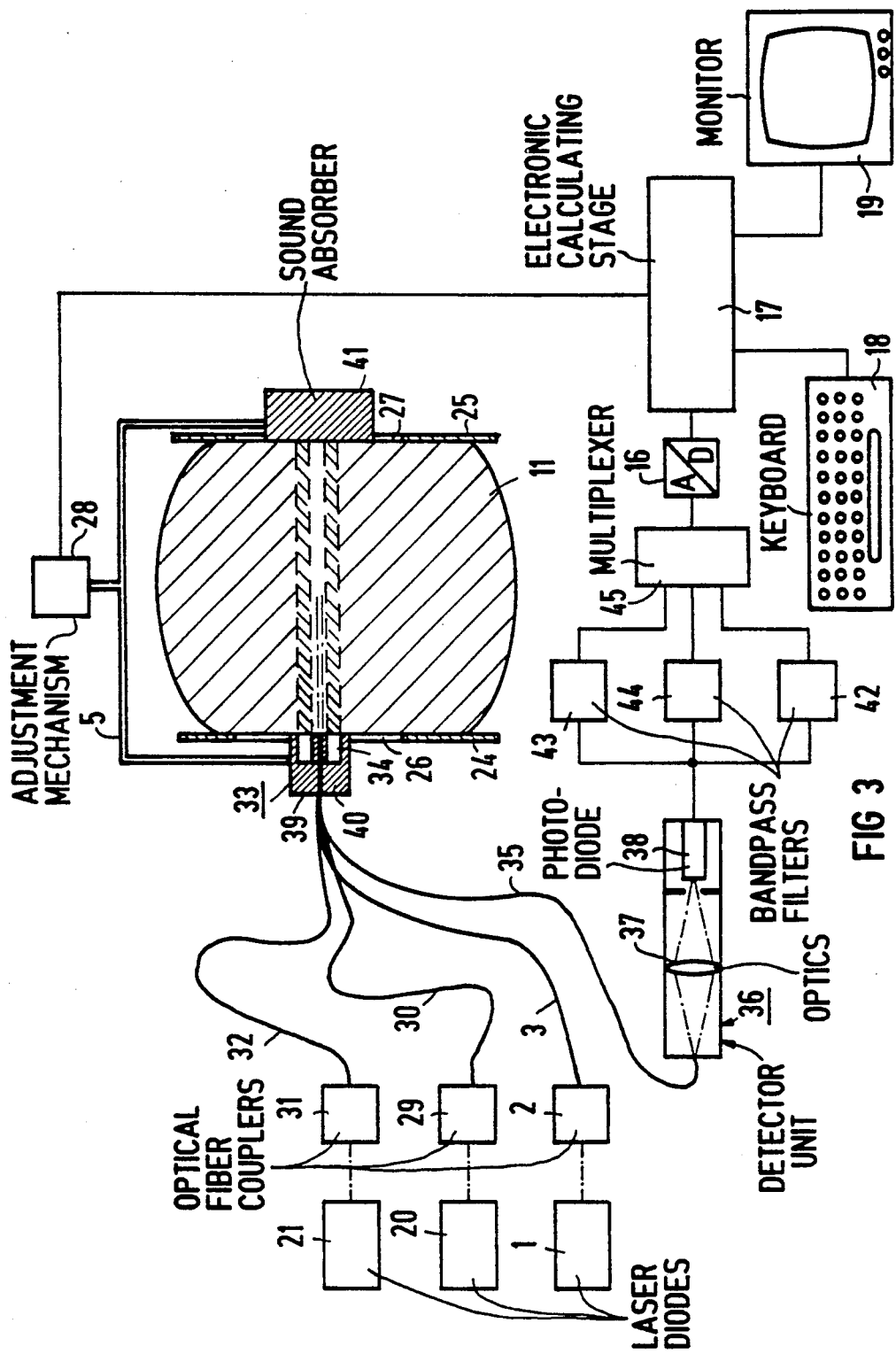
FIG. 3 shows a measuring arrangement of the invention working according to the reflection principle shown as a block circuit diagram.

The measuring arrangement of the invention shown in FIG. 3 coincides with that described above in terms of specific points, and thus respectively identical or similar elements bear the same reference characters.

Figure 4:
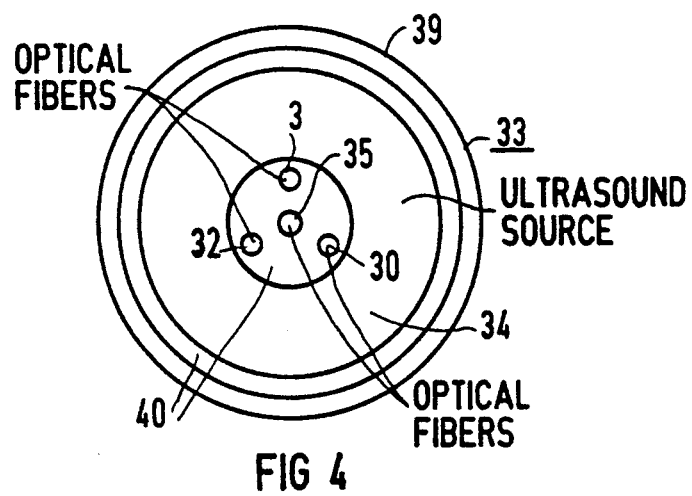
FIG. 4 shows a detail of the measuring arrangement of FIG. 3.

Three laser diodes 1, 20 and 21 are again present in the measuring arrangement of FIG. 3, respectively generating light having the wavelengths 760 nm, 800 nm and 840 nm. In addition to the optical fiber coupler 2 and the optical fiber 3 that are permanently assigned to the laser diode 1, optical fiber couplers 29 and 31 as well as optical fibers 30 and 32 connected thereto are provided. These are permanently allocated to the respective laser diodes 20 and 21. The optical fibers 3, 30 and 32 are accepted in an application head 33 that, according to FIG. 4, contains a single, circularly annular ultrasound source 34. The optical fibers 3, 30 and 32 proceed through the bore of the ultrasound source 34 such that the light rays emerging from their light exit ends proceed parallel in the absence of the subject 11.

A further optical fiber 35 serves the purpose of supplying the light emerging from the subject 11 being examined, for example a female breast, to a detector unit 36 that contains an optics 37 and a photodiode 38. Since, by contrast to the above-described measuring arrangement, it is not the light transmitted through the subject 11 but the light back-scattered from the subject 11 that is detected, the light entry end of the optical fiber 35 is also accepted in the application head 33, such that it is surrounded by the light exit ends of the optical fibers 3, 32 and 33 as can be seen from FIG. 4. The light exit ends of the optical fibers 3, 32 and 33 constitute the light exit zone of the measuring arrangement, whereas the light entry zone thereof is formed by the light entry end of the optical fiber 35. Those sections of the optical fibers 3, 32, 33 and 35 accepted in the application head 33 and connected to the light exit ends or to the light entry end proceed parallel to one another. The ends of the optical fibers 3, 32, 33 and 35 as well as the ultrasound source 34 are accepted in a pot-shaped housing 39 that is otherwise filled with a suitable casting compound 40. The dimensions of the ultrasound source 34 are again selected such that the source 34 emits ultrasound in directed fashion, namely such that a tubular region charged by ultrasound is produced in the subject 11 and within which an ultrasound-free zone Z is situated. The region charged with ultrasound is again shown in FIG. 3 by dashed, straight, parallel limiting lines and different shading. With respect to the actual shape of the region charged with ultrasound, the comments made in conjunction with FIG. 1 apply. The paths of the light emerging from the optical fibers 3, 30, 32 and of the light back-scattered in the ultrasound-free zone Z to the optical fiber 35 are respectively indicated with dot-dash lines. The application head 33 is attached to a rigid carrier 5 to which, moreover, a sound absorber 41 is attached lying opposite the application head 33. By contrast to the sound absorber 14 of the earlier described exemplary embodiment, this sound absorber 41 does not have an opening.

Since light having three different wavelengths is simultaneously directed into the subject, the light back-scattered from the subject 11 is a mixture of three optical beat signals. This is because the frequency shift exhibited by those parts of the detected light that were scattered in the region of the subject 11 charged with ultrasound is dependent on the wavelength of the scattered light. Consequently, the electrical output signal of the photodiode 38 of the detector unit 36 is also a signal mixture that corresponds to that signal that would occur in the demodulation of the mixture of beat signals. The output signal of the photodiode 38 is supplied to three band-pass filters 42, 43 and 44 connected in parallel. Their respective center frequencies are selected such that each center frequency corresponds to the beat frequency of a different optical beat signal contained in the mixture of optical beat signals. The output signals of the band-pass filters 42, 43 and 44 thus respectively deliver information about the absorption behavior of the ultrasound-free zone Z for each of the light wavelengths employed. The output signals of the band-pass filters 42, 43 and 44 are supplied to the inputs of a three-to-one analog multiplexer 45. The output thereof is connected to the input of the analog-to-digital converter 16. The digital output data of the analog-to-digital convecter 16 are supplied to the electronic calculating stage 17 to which the keyboard 18 and the monitor 19 are again connected. The adjustment mechanism 28 connected to the frame 5 is also connected to the electronic calculating stage 17. The adjustment mechanism 28 adjusts the frame 5 with the application head 33 and the sound absorber 41 in the way set forth in conjunction with FIG. 1 for implementing a scan motion. The electronic calculating stage 17 stores the data arising during the course of this scan motion and processes them as described above to form the absorption arrays allocated to the individual wavelengths which are numerically or graphically displayed with the monitor 19.

The band-pass filters 42, 43 and 44 as well as the multiplexer 45 can be eliminated if an optical filter means is provided (in a way not shown), which allows optical filters to be introduced in front of the photodiode 38 in alternation, their filter effect being respectively selected such that each filter allows one of the employed wavelengths to pass. Three filters matched to the employed wavelengths must then be present in a measuring arrangement according to FIG. 3, these three filters, under the control of the electronic calculating stage 17, being successively brought into the beam path of every position of the scan motion. Alternatively, there is also the possibility of providing a separate detector unit for each of the employed wavelengths, each of these separate detector units being constructed like the detector unit 36 but additionally containing an optical filter matched to the respective wavelength. The back-scattered light picked up with the optical fiber 35 can be supplied to the detector units via a suitable beam splitter. The output signals of the photodiodes of the detector unit would be supplied to the analog-to-digital converter 16 via a three-to-one analog multiplexer. Finally, there is also the possibility of directly supplying the output signal of the laser diode 38 to the analog-to-digital converter 16 when, controlled by the electronic calculating stage 17, the laser diodes 1, 20 and 21 are individually, successively activated for every position of the scan motion.

In the case of FIG. 1, the detector unit 6 need not necessarily be attached to the carrier 5. In a manner analogous to FIG. 3, an optical fiber can be provided that supplies the light emerging from the subject 11 to the detector unit. The optical fiber would then extend through an opening provided in the sound absorber attached to the carrier 5. It is also possible to arrange the laser diodes 1, 20, 21 closely adjacent to the surface of the subject in the application head and to activate the respectively desired laser diode. This offers the advantage that the optical fiber coupler 2, the optical fiber 3 and the adjustment mechanism 23, or the optical fiber couplers 2, 29, 31 and the optical fibers 3, 30, 32 can be eliminated.

The scan motion set forth in conjunction with the exemplary embodiments is intended only as an example. Other scan motions are also possible. Particularly for the measuring arrangement working in transmission mode, it can be expedient to conduct the light exit zone and the light entry zone around the subject 11 in steps on a circular path. The data obtained in this way can be processed with the electronic calculating stage according to an algorithm that corresponds to the algorithm employed in x-ray computer tomography. Tomograms of the scanned slice of the subject 11 can then be produced. Moreover, in the described exemplary embodiments, laser diodes are provided as light sources, however, it is also possible to employ gas or solid state lasers.

Wavelengths other than those light wave lengths cited in conjunction with the exemplary embodiments can be used. The entire wavelength range cited at the outset is potentially useable, dependent on the examination.

Although modifications and changes may be suggested by those skilled in the art, it is the intention of the inventor to embody within the patent warranted hereon all changes and modifications as reasonably and properly come within the scope of the inventor's contribution to the art.

I claim as my invention:

1. An arrangement for optically analyzing tissue comprising:
    light source means for directing light, selected from the group consisting of visible light, infrared light and near-infrared light, along an optical axis at a tissuecontaining subject,
    detector means for detecting light from said light source means emerging from said subject and for generating electrical signals corresponding thereto;
    ultrasound source means for directing ultrasound at said subject along an acoustic axis, said ultrasound interacting with some of said tissue in said subject so that said subject has tissue charged with ultrasound and tissue not charged with ultrasound;

said light source means and said ultrasound source means being disposed so that said optical axis and said acoustic axis are substantially parallel in said subject; and evaluation means supplied with said signals from said detector means for separately calculating each of the intensity of light emerging from said subject which has passed through said tissue charged with ultrasound and the intensity of light emerging from said subject which has passed through said tissue not charged with ultrasound.

2. An arrangement as claimed in claim 1 wherein said evaluation means is a means for calculating absolute intensity of said light emerging from said subject which has passed through said tissue charged with ultrasound and absolute intensity of said light emerging from said subject which has passed through said tissue not charged with ultrasound.

3. An arrangement as claimed in claim 1 wherein said evaluation means is a means for calculating relative intensities of said light emerging from said subject which has passed through said tissue charged with ultrasound and said light emerging from said subject which has passed through said tissue not charged with ultrasound.

4. An arrangement as claimed in claim 3 wherein said evaluation means includes means for forming the quotient of said intensities.

5. An arrangement as claimed in claim 1 wherein said ultrasound source means comprises a plurality of individual ultrasound generators.

6. An arrangement as claimed in claim 5 wherein said individual ultrasound generators are arranged to generate a region in said subject of said tissue charged with ultrasound surrounding a substantially ultrasound-free zone containing said tissue not charged with ultrasound, and wherein said light source means and said ultrasound source means are oriented so that said optical axis proceeds through said ultrasound-free zone.

7. An arrangement as claimed in claim 5 wherein said individual ultrasound generators are annularly arranged.

8. An arrangement as claimed in claim 1 wherein said ultrasound source means is a means for generating an annular ultrasound field in said examination subject having a center axis which is said acoustic axis, and wherein said light source means and said ultrasound source means are oriented so that said optical axis proceeds along said center axis.

9. An arrangement as claimed in claim 1 further comprising:

a sound absorber disposed substantially in registry with and at a side of said subject opposite to said ultrasound source means for absorbing ultrasound from said ultrasound sound source emerging from said subject.

10. An arrangement as claimed in claim 1 wherein said light source means comprises a laser diode.

11. An arrangement as claimed in claim 1 further comprising:

light guide means for guiding light from said light source means to said subject.

12. An arrangement as claimed in claim 11 wherein said light guide means is a fiber-optical light guide means.

13. An arrangement as claimed in claim 1 further comprising:

light guide means for guiding said light emerging from said subject to said detector means.

14. An arrangement as claimed in claim 13 wherein said light guide means is a fiber-optical light guide means.

15. An arrangement as claimed in claim 1 wherein said detector means includes a photomultiplier for generating said electrical signals.

16. An arrangement as claimed in claim 1 wherein said detector means includes a photodiode for generating said electrical signals.

17. An arrangement as claimed in claim 1 wherein said light source means has a light exit zone from which light directed to said subject exits and wherein said detector means has a light entry zone in to which said light emerging from said subject enters, and said arrangement further comprising:

means for mounting said light entry zone and said light exit zone opposite each other with said subject therebetween; and means for generating a relative movement between said light entry and exit zones and said subject for optically scanning said subject.

18. An arrangement as claimed in claim 1 wherein said light source means has a light exit zone from which light directed to said subject exits and wherein said detector means has a light entry zone into which said light emerging from said subject enters, and said arrangement further comprising:

means for mounting said light exit zone and said light entry zone in close proximity to each other adjacent said subject; and means for generating a relative movement between said light entry and exit zones and said subject for optically scanning said subject.

19. An arrangement as claimed in claim 17 or 18 wherein said evaluation means includes means for calculating an at least two-dimensional absorption array of absorption coefficients of a scanned region of said subject.

20. An arrangement as claimed in claim 19 wherein said evaluation means includes graphic display means for displaying the calculated absorption arrays with different chromatic values allocated to different absorption coefficients.

21. An arrangement as claimed in claim 19 wherein said evaluation means includes graphic display means for displaying the calculated absorption arrays with different grayscale values allocated to different absorption coefficients.

22. An arrangement as claimed in claim 1 wherein said light source means includes a plurality of light sources respectively generating light of different wavelengths and means for selecting one of said light sources at a time for directing light at said subject.

23. An arrangement as claimed in claim 1 wherein said light source means includes a plurality of light sources respectively generating light of different wavelengths, and means for simultaneously directing light from said light sources at said subject.

24. An arrangement as claimed in claim 23 wherein said detector means includes means for simultaneously detecting light of said different wavelengths emerging from said subject.

25. A method for optically analyzing tissue comprising the steps of:

directing light, selected from the group consisting of visible light, infrared light and near-infrared light, along an optical axis at a tissue-containing subject, detecting light from said light source means emerging from said subject and generating electrical signals corresponding thereto;

directing ultrasound at said subject along an acoustic axis, said ultrasound interacting with some of said tissue in said subject so that said subject has tissue charged with ultrasound and tissue not charged with ultrasound;

disposing said light source means and said ultrasound source means so that said optical axis and said acoustic axis are substantially parallel in said subject; and separately calculating each of the intensity of light emerging from said subject which has passed through said tissue charged with ultrasound and the intensity of light emerging from said subject which has passed through said tissue not charged with ultrasound.

26. A method as claimed in claim 25 wherein the step of calculating the intensity is further defined by calculating the absolute intensity of said light emerging from said subject which has passed through said tissue charged with ultrasound and the absolute intensity of said light emerging from said subject which has passed through said tissue not charged with ultrasound.

27. A method as claimed in claim 25 wherein the step of calculating the intensity is further defined by calculating the relative intensities of said light emerging from said subject which has passed through said tissue charged with ultrasound and said light emerging from said subject which has passed through said tissue not charged with ultrasound.

28. A method as claimed in claim 27 comprising the additional step of forming the quotient of said intensities.

29. A method as claimed in claim 25 wherein the step of directing ultrasound at said subject is further defined by arranging a plurality of individual ultrasound generators to generate a region in said subject of said tissue charged with ultrasound surrounding a substantially ultrasound-free zone containing said tissue not charged with ultrasound, and orienting said light source means and said ultrasound source means so that said optical axis proceeds through said ultrasound-free zone.

30. A method as claimed in claim 29 wherein the step of directing ultrasound at said subject is further defined by annularly arranging said individual ultrasound generators.

31. A method as claimed in claim 25 wherein the step of directing ultrasound at said subject is further defined by generating an annular ultrasound field in said examination subject having a center axis which is said acoustic axis, and orienting said light source means and said ultrasound source means so that said optical axis proceeds along said center axis.

32. A method as claimed in claim 25 comprising the additional step of:
absorbing ultrasound emerging from said subject with a sound absorber.

33. A method as claimed in claim 25 wherein the step of directing light at a tissue-containing subject is further defined by directing light from a laser diode at said tissue-containing subject.

34. A method as claimed in claim 25 comprising the additional step of:
guiding light to said subject via a light guide.

35. A method as claimed in claim 34 wherein the step of guiding said light is further defined by guiding said light to said subject via a fiber-optical light guide.

36. A method as claimed in claim 25 comprising the additional step of:
guiding said light emerging from said subject to a detector.

37. A method as claimed in claim 36 wherein the step of guiding said light is further defined by guiding said light emerging from said subject to a detector via a fiberoptical light guide means.

38. A method as claimed in claim 25 wherein the step of generating said electrical signals is further defined by generating said electrical signals with a photomultiplier.

39. A method as claimed in claim 25 wherein the step of detecting said light is further defined by detecting said light with a photodiode.

40. A method as claimed in claim 25 wherein the step of directing light at a tissue-containing subject is further defined by emitting said light from a light exit zone from which light directed to said subject exits and wherein the step of detecting said light is further defined by detecting said light via a light entry zone into which said light emerging from said subject enters, and comprising the additional steps of:

mounting said light entry zone and said light exit zone opposite each other with said subject therebetween; and generating a relative movement between said light entry and exit zones and said subject for optically scanning said subject.

41. An arrangement as claimed in claim 25 wherein the step of directing light at a tissue-containing subject is further defined by emitting said light from a light exit zone from which light directed to said subject exits and wherein the step of detecting said light is further defined by detecting said light via a light entry zone into which said light emerging from said subject enters, and comprising the additional steps of:

mounting said light exit zone and said light entry zone in close proximity to each other adjacent said subject; and generating a relative movement between said light entry and exit zones and said subject for optically scanning said subject.

42. A method as claimed in claim 40 or 41 comprising the additional step of calculating an at least two-dimensional absorption array of absorption coefficients of a scanned region of said subject.

43. A method as claimed in claim 42 comprising the additional step of displaying the calculated absorption arrays with different chromatic values allocated to different absorption coefficients.

44. A method as claimed in claim 42 comprising the additional step of displaying the calculated absorption arrays with different grayscale values allocated to different absorption coefficients.

45. A method as claimed in claim 25 wherein the step of directing light at said tissue-containing subject is further defined by selecting one from a plurality of light sources respectively generating light of different wavelengths at a time for directing light at said subject.

46. A method as claimed in claim 25 wherein the step of directing light at said tissue-containing subject is further defined by simultaneously directing light from a plurality of light sources respectively generating light of different wavelengths at said subject.

47. A method as claimed in claim 46 wherein the step of detecting light is further defined by simultaneously detecting light of said different wavelengths emerging from said subject.

* * * * *